US008784307B1

(12) United States Patent
Groteke et al.

(10) Patent No.: US 8,784,307 B1
(45) Date of Patent: Jul. 22, 2014

(54) INTEGRATIVE BIOMECHANICAL ANALYSIS

(76) Inventors: Eric K. Groteke, Safety Harbor, FL (US); Harry Chororos, Sarasota, FL (US); Scott Miller, Apollo Beach, FL (US)

( * ) Notice: Subject to any disclaimer, the term of this patent is extended or adjusted under 35 U.S.C. 154(b) by 1314 days.

(21) Appl. No.: 12/009,902

(22) Filed: Jan. 23, 2008

Related U.S. Application Data

(60) Provisional application No. 60/897,031, filed on Jan. 23, 2007, provisional application No. 60/897,030, filed on Jan. 23, 2007.

(51) Int. Cl.
*A61B 5/00* (2006.01)
*G01N 33/48* (2006.01)
*G01N 33/50* (2006.01)

(52) U.S. Cl.
USPC ............... 600/300; 600/301; 702/19; 702/20; 702/21

(58) Field of Classification Search
USPC ................................ 600/300–301; 702/19–21
See application file for complete search history.

(56) References Cited

U.S. PATENT DOCUMENTS

| 7,146,205 | B2 * | 12/2006 | Holman | 600/515 |
| 7,149,756 | B1 * | 12/2006 | Schmitt et al. | 1/1 |
| 7,273,454 | B2 * | 9/2007 | Raymond et al. | 600/301 |
| 7,374,536 | B1 * | 5/2008 | Taylor | 600/300 |
| 8,021,298 | B2 * | 9/2011 | Baird et al. | 600/300 |
| 8,092,380 | B2 * | 1/2012 | Rothman et al. | 600/300 |
| 8,185,458 | B2 * | 5/2012 | Schmotzer | 705/35 |
| 2003/0139652 | A1 * | 7/2003 | Kang et al. | 600/300 |
| 2003/0233053 | A1 * | 12/2003 | Woolf et al. | 600/553 |

* cited by examiner

*Primary Examiner* — Gary Jackson
*Assistant Examiner* — Shirley Jian
(74) *Attorney, Agent, or Firm* — The Webb Law Firm (57) ABSTRACT

The invention is a method and system for functional biomechanical analysis. The analysis assesses the biomechanical relationships of the spine and adjacent regions in a dynamic state based on a patient's chief complaint and clinical presentation. The analysis calculates a value of function or impact for a particular spinal region.

9 Claims, 2 Drawing Sheets

INTEGRATIVE BIOMECHANICAL ANALYSIS

CROSS REFERENCE TO RELATED APPLICATIONS

This application claims the benefits of U.S. Provisional Application No. 60/897,030, filed Jan. 23, 2007, and U.S. Provisional Application No. 60/897,031, filed Jan. 23, 2007, which are hereby incorporated by reference in their entireties.

BACKGROUND OF THE INVENTION

1. Field of the Invention

This invention relates to a system and method for functional biomechanical analysis. The analysis assesses the biomechanical relationships of the spine and adjacent regions in a dynamic state based on a patient's chief complaint and clinical presentation. The analysis calculates a value of function or impact for a particular spinal region.

2. Brief Description

Many health care professionals must work around the constraints of being "second guessed" relative to an insurance reimbursement for patient care. The fact remains that the longer the treatment the more expensive the care and the more expensive the case for both insurer and patient. Managed care made its mark a long time ago by exposing healthcare "professionals" who prolonged their treatments for financial incentive. Sadly, this still happens today.

For most other segments of the healthcare industry, managed care has obligated the healthcare professionals to respond to being second guesses by creating standards of care guidelines, capturing statistical treatment data and generating metrics and measures designed to show their commitment to delivering quality patient care in a cost effective and clinically efficacious manner. Yet, few standardized measures are available for Chiropractors and many other medical professionals dealing with pain management to support their treatment plans approaches and visit number requests.

Arguing for chiropractic or physical therapy visit extensions with insurers means being prepared to defend clinical inquiries about patient care and necessity. And, as often happens, gaining an approval for a complete treatment plan may well depend more upon the chiropractor's savvy in knowing the patient's plan rather than a sound clinical skill set. This is one reason cash plans are so often sold to patients: The patient and his healthcare provider do not have to deal with the constraints of second guessing treatment plans.

If evidence-based, multi-disciplinary clinical communications data on musculoskeletal disorders (MSD) were quickly available, easily read and understood by all involved in patient care, then it could enhance chiropractor, insurer and patient communication.

All MSD conditions emanate and escalate from some type of physical trauma to a body region or body part—whether the trauma is caused by a sudden event or cumulatively generated. Adding the understanding that our musculoskeletal system functions with a high degree of bio-mechanical interrelation, it follows that an inherent physical weakness in a particular body region will increase the chances of an MSD developing in the body parts and joints of the afflicted body region.

Similarly, weakness in a particular body part or joint can often cause another stronger, but related body part to become overworked by compensating for the weakness. For example, repetitious overwork is one the most major risk factor for all MSD's. This type of reasoning could be used to support reimbursable office visits and approve complete treatment plans.

Stated succinctly; identifying inherent weaknesses in a specific body region will greatly increase the potential to identify a specific MSD concern for the body parts of that region and all bio-mechanically related areas. If this type of information could easily be shown it would allow Chiropractors to identify body regions and body parts that could well become injured because of their "compensating" for an inherent weakness elsewhere in the body.

An example would be an inherent weakness identified in a woman's left hip as the possible root cause of a problem in her knee, foot or ankle—on either side of her body. A complete treatment plan would ensure the hip flexors are strengthened to the point of releasing any dependence on any related biomechanical pathways; not just treating the pain in the left hip. Yet, without clear and excellent documentation using a standardized approach, the risk of being second guessed to only treat the pain is very likely to happen.

Merely knowing that related physical stress factors can cause an MSD, the ability to effectively document and present these findings in a manner that can be easily grasped by any "second guessers". An evidence based program that uses multi-discipline research to offer a significant pathway toward gaining clinical necessary and credibility between all parties involved.

Musculoskeletal Disorder Reporting (MSDR) is one such evidence based, multi-disciplinary approach. It is a program that analyzes a person's physical functionality using a large body of evidence-based, multi-disciplinary research sources from which clinical pathways relating to musculoskeletal conditions have been extracted and correlated. The program quantifies a persons' functionality by body region within a particular diagnosis and analyzes relationships between the joints and spine, systemic and sensory issues, BMI, and, biomechanical factors.

The MSDR approach is especially sensitive to non-acute or sub-clinical injuries such as—backs, necks, shoulders, wrists, and legs, which are the highest grouping of all occupational injuries. As these asymptomatic injuries are not at all immediately apparent and build over time with increasingly immobilizing pain along, establishing a musculoskeletal baseline exam (that is performed consistently every time) allows one to abate a potential future injury by creating awareness on their weakest area and knowing their exacerbating factors. This can avoid a multitude of costly exposures and future injury.

Output reports are by individual body region and on a total body basis. Supporting research for MSDR is preferably exclusively peer-reviewed research findings from a large library of clinical references.

MSDR was founded on analyzing history and physical correlative medical pathways for the purpose of detecting injuries before they occur. MSDR was architected to detect risk factors associated with musculo-skeletal condition in an individual with or without pain.

The MedAppraise MSDR® (MSDR®) exam is one such MSDR that provides an assessment of a patient's musculoskeletal system toward establishing a standardized musculoskeletal baseline that can be an effective "360 degree" communications tool for the chiropractic physician with insurers, case managers and patients. MSDR® is a predictive risk assessment tool for the Musculoskeletal system. The key advantage in applying an MSDR® score lies in its ability to standardize testing for musculoskeletal disorders without concern for inter-examiner reliability issues which is the fundamental basis for "second guessing" any care delivery plan. MSDR® is a predictive risk assessment tool for the Musculoskeletal system The low cost of implementation for MSDR® compared to other methods can generate a strong return-on-investment for chiropractic providers of post-analysis intervention programs for supporting and documenting treatment plans programs and their associated visit frequency.

MSDR® has been designed against "Gold Standard Tests" and "Reference Standard Findings" of a physician's exam. While highly accurate in its findings, MSDR® is not intended, nor should it be used in place of a chiropractic physician's exam.

MSDR® serves as a treatment guidance tool that can follow the injury trend of an individual regarding a specific MSD condition so a specific intervention (preventative or reactive) can be considered and applied prior to that condition growing more serious. As such, MSDr® serves as a preferred musculoskeletal baseline analysis.

This invention relates to a system and method suitable for assessing and communicating musculoskeletal disorder risks to a wide range of medical and human resource professionals.

OBJECTS OF THE INVENTION

An objective of the present invention is to provide an integrative biomechanical analysis, preferably of the MSDR approach to medical professionals for assessing a patient's MSD risk. Another objective of the present invention is to provide medical professionals an inexpensive method for assessing a patients MSD risk that is standardized and reliable.

SUMMARY OF THE INVENTION

The basic analysis process considers answers to a self-administered medical and personal history questionnaire along with objective results obtained by a Biometric Analysis. The total question set (personal history, medical history and Biometric results) is reviewed as a whole to determine the initial risk score. After then identifying the participant's chief complaint and primary area of involvement, it is reviewed to identify complicating factors in the form of Bio mechanics (joints and spine) and Sensory (nerves) issues.

The final part of the analysis looks at systemic issues and responses which will "Trump" all calculations. The resulting score is a comprehensive analysis of the musculoskeletal system and risks associated with lifestyle, personal medical history and objective measurements obtained during the Biometric testing.

The analysis assesses the biomechanical relationships of the spine and adjacent regions in a dynamic state based on a patient's chief complaint and clinical presentation. The analysis calculates a value of function or impact for a particular spinal region.

The MSDR Analysis when used in conjunction with physical health assessments can detect changes in spinal function as it relates to other regions of the spine and the surrounding regions when clinically necessary.

The MSDR Analysis assesses a "functional value" on biomechanical impact on the spine based on a participants' function within that particular region.

The MSDR Analysis Process begins with an initial review of the priority region(s) of involvement through identifying the Chief Complaint(s) through detection of the primary primary joint of involvement within the primary area of involvement. A calculation of the initial regional score is obtained through group responses by region and compared to all the regions of the body (Neck, Upper Extremities, Back, and Lower Extremities). A resultant weighted average is calculated for each region. Initial regional scores are correlated with complicating factors (Direct and Indirect Risk factors), along with biomechanical analyses and other pertinent complicated factors such as BMI (in weight bearing joints only) to result in an overall joint score that is grouped for the effected region.

Spinal analysis is performed for each spinal region, then correlated with inter-regional relationships ie. Lumbar discogenic syndrome with radiculopathy affecting the back and lower extremity. Examples of inter-regional relationships can be spinal nerves effecting the extremities, or an altered gait pattern yielding a biomechanical dysunction from a previous surgery in the hip or knee.

Sensory and possible systemic findings are superimposed on biomechanical analyses and compound region of involvement impact. Lastly, a final region score is given after medical correlative algorithms are reference against pertentent medical history and Activities of Daily Living functions.

The scores in one preferred embodiment are stratified on a scale with a starting point at 100 and an ending point of 399. Low stratification consists of 100-199, Medium stratification ranges from 200-299, and High Stratification ranges from 300-399. The final factoring score is converted to the corresponding value that is displayed on the MSDR scale.

MSDR Best Clinical Practice Methods include historical ADL gathering with O, P, Q, R, S, T format. OPQRST is a medical history taking pneumonic that stands for Onset, Palliative/Provacative, Quality of Symptom(s), Radiation of Symptom(s), Site/Severity, and Timing of Symptom(s). Clinical categorization of traditional medical MS history is grouped into areas of involvement (Single or Multi-focal); quality of symptoms (Stiffness, Numbness/tingling, Dull ache, Burning, Sharp); Frequency of symptoms (Daily, Weekly, Monthly); Severity (Treatment: Non-surgical vs. Surgical; Visual Analogue Scale Rating). A Biometric exam which is a progressive physical examination involving, static structural testing and dynamic testing (self range of motion movements and/or self orthopedic/neurological testing.

The MSDR findings are reported in the form of the Individual Report of Findings (for the end user), the Clinical Snapshot (for the healthcare provider), and the Decision Support Worksheet (DSW) for internal auditing and quality assurance purposes.

The concept of flexibility testing is often used in physical therapy and chiropractic practices (see Cox and Liebenson References) for quantification of findings in a pass/fail environment. MSDR utilizes this concept with provocative testing to obtain data from the individual for the purpose of quantifying their findings for a particular body region and reporting back to them in the above mentioned reports.

High risk regions are those areas with symptoms and pain. Individuals in the low risk and low medium range comprise those without pain and symptoms. This real time assessment allows the examiner to correlate the consistency between subjective and objective findings, in order to better manage a person's musculoskeletal findings for the purpose of treatment and/or prevention, Additionally, the organization of positive historical, ADL's, work, home, sports or activity related events to physical findings provides a clinical snapshot, enabling the examiner to correlate, educate, and better manage and prioritize an individual's regional or whole person intervention plan.

MSDR has the ability to quantify MS findings with or without symptoms. This allows a Healthcare Provider to objectively quantify patient improvement following symptom resolution and documents the value of a chiropractic wellness plan, maintaining function, in an asymptomatic state and prevents an individual from "trending in the wrong direction."

The invention, a system and method for functional biomechanical analysis, could be used in the clinical setting or as human resource tool for assessing MSD risk. The invention could be used and modified to assess risk for any MS disease or disorder. The values and assumptions of the present invention could be changed as new knowledge and understanding developed in the medical field.

In one embodiment the invention is a method of assessing musculoskeletal disorder risk, comprising the steps of: providing a questionnaire that contains at least one question in regard to location of pain; recording a response to said at least one question in said questionnaire; providing a matrix of relationships and values that assigns a level of impact to at least one body region from said responses from said at least one question; calculating a weighted average of level of impact for said at least one body region; generating a scaled score from said weighted average of level of impact for at least one body region.

In one embodiment the invention is a method of assessing musculoskeletal disorder risk, comprising the steps of: providing a questionnaire that contains at least one question in regard to location of pain; recording a response to said at least one question in said questionnaire; providing a matrix of relationships and values that assigns a level of impact to at least one body region from said responses from said at least one question; calculating a weighted average of level of impact for said at least one body region; generating a scaled score from said weighted average of level of impact for at least one body region; suggesting a treatment to reduce a musculoskeletal disorder risk based on at least in part on said scaled score.

In one embodiment the invention is a method of assessing musculoskeletal disorder risk, comprising the steps of: providing a questionnaire that contains at least one question in regard to location of pain and at least one question in regard to level of pain; recording a response to said at least one question in said questionnaire; providing a matrix of relationships and values that assigns a level of impact to at least one body region from said responses from said at least one question; calculating a weighted average of level of impact for said at least one body region; generating a scaled score from said weighted average of level of impact for at least one body region.

In one embodiment the invention is a method of assessing musculoskeletal disorder risk, comprising the steps of: providing a questionnaire that contains at least one question in regard to location of pain and at least one question in regard to quality of pain; recording a response to said at least one question in said questionnaire; providing a matrix of relationships and values that assigns a level of impact to at least one body region from said responses from said at least one question; calculating a weighted average of level of impact for said at least one body region; generating a scaled score from said weighted average of level of impact for at least one body region.

In one embodiment the invention is a method of assessing musculoskeletal disorder risk, comprising the steps of: providing a questionnaire that contains at least one question in regard to location of pain and at least one question in regard to frequency of pain; recording a response to said at least one question in said questionnaire; providing a matrix of relationships and values that assigns a level of impact to at least one body region from said responses from said at least one question; calculating a weighted average of level of impact for said at least one body region; generating a scaled score from said weighted average of level of impact for at least one body region.

In one embodiment the invention is a method of assessing musculoskeletal disorder risk, comprising the steps of: providing a questionnaire that contains at least one question in regard to location of pain; recording a response to said at least one question in said questionnaire; providing a matrix of relationships and values that assigns a level of impact to at least one body region from said responses from said at least one question; calculating a weighted average of level of impact for said at least one body region; generating a scaled score from said weighted average of level of impact for at least one body region; wherein the method yields a quantification of musculoskeletal disorder risk within a body region.

In yet another embodiment the invention is a method of assessing musculoskeletal disorder risk, comprising the steps of: providing a questionnaire that contains at least one question in regard to location of pain; recording responses to said at least one question in said questionnaire; providing a set of integration grids that assign a level of impact to at least one body region from said responses from said at least one question; calculating a weighted average of level of impact for said at least one body region; generating a scaled score from said weighted average of level of impact for at least one body region.

In yet another embodiment the invention is a method of assessing musculoskeletal disorder risk, comprising the steps of: providing a questionnaire that contains at least one question in regard to location of pain; recording responses to said at least one question in said questionnaire; providing a set of integration grids that assign a level of impact to at least one body region from said responses from said at least one question; calculating a weighted average of level of impact for said at least one body region; generating a scaled score from said weighted average of level of impact for at least one body region; wherein the method yields a quantification of musculoskeletal disorder risk within a body region.

In yet another embodiment the invention is a method of assessing musculoskeletal disorder risk, comprising the steps of: providing a questionnaire that contains at least one question in regard to location of pain; recording responses to said at least one question in said questionnaire; providing a set of integration grids that assign a level of impact to at least one body region from said responses from said at least one question; calculating a weighted average of level of impact for said at least one body region; generating a scaled score from said weighted average of level of impact for at least one body region; wherein said set of integration grids allows for assessing relationships between body regions.

In yet another embodiment the invention is a method of assessing musculoskeletal disorder risk, comprising the steps of: providing a questionnaire that contains at least one question in regard to location of pain; recording responses to said at least one question in said questionnaire; providing a set of integration grids that assign a level of impact to at least one body region from said responses from said at least one question; calculating a weighted average of level of impact for said at least one body region; generating a scaled score from said weighted average of level of impact for at least one body region; wherein said set of integration grids allows for assessing relationships within body regions.

In yet another embodiment the invention is a method of assessing musculoskeletal disorder risk, comprising the steps of: providing a questionnaire that contains at least one question in regard to location of pain; recording responses to said at least one question in said questionnaire; providing a set of integration grids that assign a level of impact to at least one body region from said responses from said at least one question; calculating a weighted average of level of impact for said at least one body region; generating a scaled score from said weighted average of level of impact for at least one body region; wherein said set of integration grids allows for assessing relationships between and within body regions.

In still yet another embodiment the invention is a method of assessing musculoskeletal disorder risk, comprising the steps of: providing a questionnaire that contains at least one question in regard to location of pain, at least one question in regard to level of pain, at least one question in regard to quality of pain, and at least one question in regard to frequency of pain; recording responses to said questions in said questionnaire; providing a set of integration grids that assign a level of impact to at least one body region from said responses; calculating a weighted average of level of impact for said at least one body region; generating a scaled score from said weighted average of level of impact for at least one body region.

In still yet another embodiment the invention is a method of assessing musculoskeletal disorder risk, comprising the steps of: providing a questionnaire that contains at least one question in regard to location of pain, at least one question in regard to level of pain, at least one question in regard to quality of pain, and at least one question in regard to frequency of pain; recording responses to said questions in said questionnaire; providing a set of integration grids that assign a level of impact to at least one body region from said responses; calculating a weighted average of level of impact for said at least one body region; generating a scaled score from said weighted average of level of impact for at least one body region; wherein said set of integration grids allows for assessing relationships between and within body regions.

In still yet another embodiment the invention is a method of assessing musculoskeletal disorder risk, comprising the steps of: providing a questionnaire that contains at least one question in regard to location of pain, at least one question in regard to level of pain, at least one question in regard to quality of pain, and at least one question in regard to frequency of pain; recording responses to said questions in said questionnaire; providing a set of integration grids that assign a level of impact to at least one body region from said responses; calculating a weighted average of level of impact for said at least one body region; generating a scaled score from said weighted average of level of impact for at least one body region; wherein the method yields a quantification of musculoskeletal disorder risk within a body region.

In still yet another embodiment the invention is a method of assessing musculoskeletal disorder risk, comprising the steps of: providing a questionnaire that contains at least one question in regard to location of pain, at least one question in regard to level of pain, at least one question in regard to quality of pain, and at least one question in regard to frequency of pain; recording responses to said questions in said questionnaire; providing a set of integration grids that assign a level of impact to at least one body region from said responses; calculating a weighted average of level of impact for said at least one body region; generating a scaled score from said weighted average of level of impact for at least one body region; suggesting a treatment to reduce a musculoskeletal disorder risk based on at least in part on said scaled score.

In still yet another embodiment the invention is a method of assessing musculoskeletal disorder risk, comprising the steps of: providing a questionnaire that contains at least one question in regard to location of pain, at least one question in regard to level of pain, at least one question in regard to quality of pain, and at least one question in regard to frequency of pain; recording responses to said questions in said questionnaire; providing a set of integration grids that assign a level of impact to at least one body region from said responses; calculating a weighted average of level of impact for said at least one body region; generating a scaled score from said weighted average of level of impact for at least one body region; wherein the method yields a quantification of musculoskeletal disorder risk within a body region; wherein the step of providing a questionnaire additionally contains at least one question in regard to sensory symptoms.

In still yet another embodiment the invention is a method of assessing musculoskeletal disorder risk, comprising the steps of: providing a questionnaire that contains at least one question in regard to location of pain, at least one question in regard to level of pain, at least one question in regard to quality of pain, and at least one question in regard to frequency of pain; recording responses to said questions in said questionnaire; providing a set of integration grids that assign a level of impact to at least one body region from said responses; calculating a weighted average of level of impact for said at least one body region; generating a scaled score from said weighted average of level of impact for at least one body region; wherein the method yields a quantification of musculoskeletal disorder risk within a body region; wherein the step of providing a questionnaire additionally contains at least one question in regard to numbness.

In still yet another embodiment the invention is a method of assessing musculoskeletal disorder risk, comprising the steps of: providing a questionnaire that contains at least one question in regard to location of pain, at least one question in regard to level of pain, at least one question in regard to quality of pain, and at least one question in regard to frequency of pain; recording responses to said questions in said questionnaire; providing a set of integration grids that assign a level of impact to at least one body region from said responses; calculating a weighted average of level of impact for said at least one body region; generating a scaled score from said weighted average of level of impact for at least one body region; wherein the method yields a quantification of musculoskeletal disorder risk within a body region; wherein the method yields a quantification of musculoskeletal disorder risk.

In still yet another embodiment the invention is a method of assessing musculoskeletal disorder risk, comprising the steps of: providing a questionnaire that contains at least one question in regard to location of pain, at least one question in regard to level of pain, at least one question in regard to quality of pain, and at least one question in regard to frequency of pain; recording responses to said questions in said questionnaire; providing a set of integration grids that assign a level of impact to at least one body region from said responses; calculating a weighted average of level of impact for said at least one body region; generating a scaled score from said weighted average of level of impact for at least one body region; wherein the method yields a quantification of musculoskeletal disorder risk within a body region; suggesting a treatment to reduce a musculoskeletal disorder risk based on at least in part on said scaled score.

In still yet another embodiment the invention is a method of assessing musculoskeletal disorder risk, comprising the steps of: providing a questionnaire that contains at least one question in regard to location of pain, at least one question in regard to level of pain, at least one question in regard to quality of pain, and at least one question in regard to frequency of pain; recording responses to said questions in said questionnaire; providing a set of integration grids that assign a level of impact to at least one body region from said responses; calculating a weighted average of level of impact for said at least one body region; generating a scaled score from said weighted average of level of impact for at least one body region; wherein the method yields a quantification of musculoskeletal disorder risk within a body region; generating an overall scaled score from said weighted average of level of impact from a plurality of body regions.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention; and together with the description serve to explain the principles and operation of the invention.

DETAILED DESCRIPTION

Figure 1:
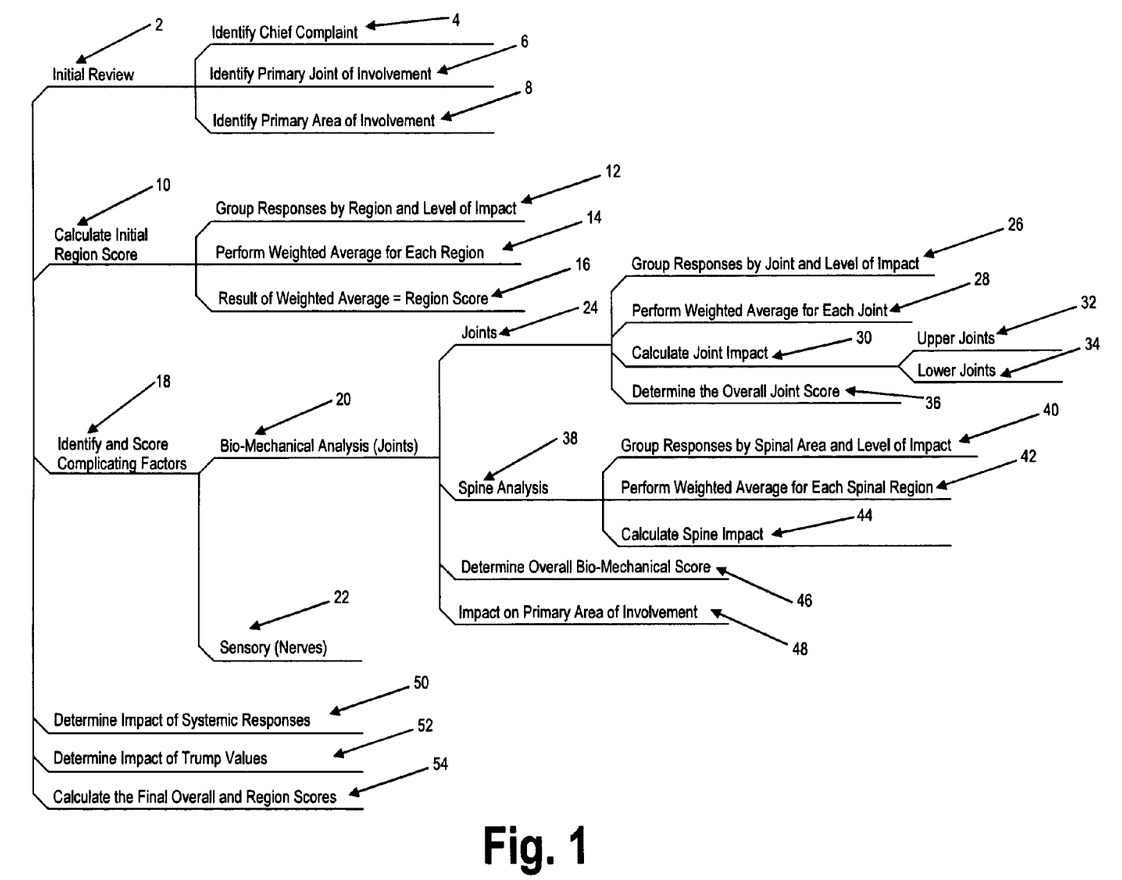
FIG. 1 shows a chart of an example analysis process of the present invention.

FIG. 1 shows an example of the analysis process of the present invention, a MSD Risk Analysis Process. The process begins with the Initial Review 2 which comprises identifying the participant's Chief Complaint 4, Primary Joint of Involvement 6, and Primary Area of Involvement 8.

To identify Chief Complaint 4, one section of the questionnaire contains an anatomic chart where the participant is asked to identify any areas of the body where they have/have had pain or treatment. They are asked to describe the pain in terms of: Level of Pain (based on the Visual Analog Scale of 0-10), If they have had Treatment/Surgery, Timing (how frequently does it occur i.e. daily, weekly, monthly), Quality of the pain (stiffness, dull, burning or sharp). The anatomical point where the participant's pain is most severe (based on VAS), had treatment/surgery, most frequent and where the quality of pain is highest is the participant's Chief Complaint 4.

To identify Primary Joint of Involvement 6 using the relationships found in a predetermined MSD matrix, identify the joint associated with the Chief Complaint 4. This joint becomes the focus of our biomechanical analysis and is identified as the Primary Joint of Involvement 6.

To identify Primary Area of Involvement 8 using the relationships found in a predetermined MSD matrix, identify the body region(s) associated with the Chief Complaint 4. The associated region(s) is the Primary Area of Involvement 8. Note: It is possible for more than one region of the body to be involved.

To calculate the Initial Region Score 10 for each body region, each possible answer in the questionnaire is associated with one or more body regions. Each unique answer/region combination is associated with a level of Impact (0, L, M or H) in the predetermined MSD Matrix. For each associated region, Group Responses by Region and Level of Impact 12. Eliminate any responses with a value of 0. Then assign a weighted value to each of the remaining answers based on their associated impact (L, M or H). Calculate the region score by performing a Weighted Average 14 and dividing that value by the total possible score. (Note: Total possible score=total number of non-zero answers for that region times the highest weight value). The resulting decimal value is translated into a score of L, M or H for that region based on defined parameters. The Overall MSD Risk score equals the highest Region Score 16.

Then Identify and Score Complicating Factors 18. There are two categories of complicating factors; Bio-Mechanical Analysis 20 (Joints/Spine) and Sensory 22 (Nerves).

Bio mechanic Analysis—Joints 24: The body is divided into Upper Joints 32 and Lower Joints 34. Within each of these two categories a Joint System is identified. Each joint within the Joint System is assigned a priority starting with the Primary Joint of Involvement. The more distal (furthest) a joint is from the Primary Joint of involvement the lower the priority. During the analysis process, additional weight is given to those joints that are closest to the Primary Joint of Involvement. Group all responses in the questionnaire by the associated joint identified 26 in the MSD Matrix. Perform a weighted average 28 (similar to the one used for the regions) on each joint. The result will be a score of L, M or H for each joint within the Joint System to find the Joint Impact 30. Apply an additional weight to the joints based on their priority. The lower the priority, the lower this weight will be. This is done for the Upper Joints 32, but in the case of the Lower Joints 34, an additional weight is used to recognize the impact of the individual's body mass index. The concept being individuals who are overweight produce more stress on the lower joints. The weight used in this calculation is a direct correlation to the ratio of their actual Body Mass Index compared to their ideal Body Mass Index (BMI).

Bio-mechanic Analysis—Spine 38: If the chief complaint involves one of the 6 defined spinal areas and there is at least 1 other positive response with a L, M, H involving the spine then an additional analysis is performed to review the spine. This analysis is performed similar to the joints. Answers are grouped by their designated Spinal Area scored with a weighted average 40. The weighted average for each spinal area is then weighted again based on the spine priority 42 to obtain the Spine Impact 44.

Overall Bio-mechanic Score 46: If the Spine Analysis was performed, then the Overall Score for the Bio-Mechanic Analysis 46 is the simple average of the Overall Joint Score 36 and the Spine Impact Score 44. If the Spine analysis is not performed, the Overall bio mechanic score 46 equals the Overall Joint score 36. The resulting decimal value is translated into a joint score of L, M or H based on defined parameters. Determine the impact of this score on the individual region and overall scores as defined later in this document to obtain Impact on Primary Area of Involvement 48.

Sensory Analysis 22: Review the questions for any responses with a correlating value in the "Sensory" column of the MSD Matrix. Review the questions for any pattern of responses related to sensory issues defined later in this document. Determine the impact of these responses on the region and overall scores as defined later in this document.

Determine the impact of Systemic Responses 50. Some of the questions in the questionnaire affect every region of the body. These questions are identified in the MSD Matrix by an "X" in the Systemic column of the MSD Matrix. Perform a weighted average of responses to these questions (similar to the one used for the regions). Determine the impact of these responses based on rules defined later in this document.

Trump Values 52. Some questions/answers are so significant they "Trump" any of the rules or calculations done thus far and impact either a region or the overall score. These questions/answers are identified in the MSD Matrix. Determine the impact of these values as defined in the MSD Matrix by the letter "T" where a value of L, M or H would be expected and also later in this document.

Determine the Final Overall & Region Scores 54. Starting with the initial Overall and Region scores: Apply the impact of the complicating factors followed by the impact of the Systemic Factors and the Trump Values. The result is the final Overall and Region Scores 54.

Provided below is an outline of example values and calculations for the above explained method and analysis. This values can be changed depending on the medical references used; application; and assumptions made to create the MSD Matrix and the Anatomic Reference Summary.

Assumptions and Properties of Analysis

There are 4 regions of the body—Neck, Upper Extremities, Back and Lower Extremities.

Each Question/Answer is assigned a risk score of 0, L, M or H

Each Question/Answer is associated with one or more of the 4 regions.

Each Question/Answer is also associated with a Joint System

Figure 2:
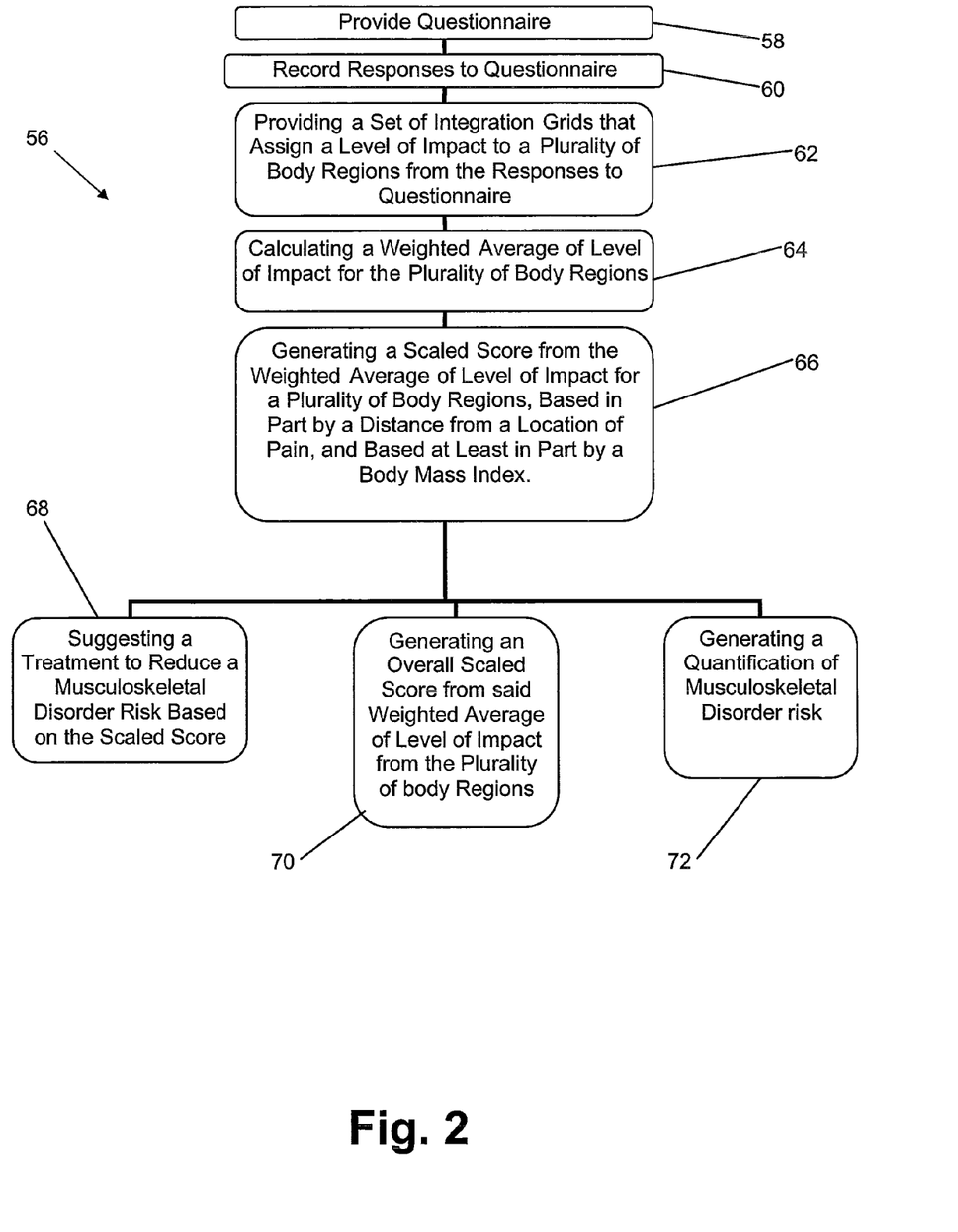
FIG. 2 shows a flowchart detailing a method of assessing musculoskeletal disorder risk according to an embodiment of the present invention.

FIG. 2 shows a flowchart detailing a method of assessing musculoskeletal disorder risk 56 according to an embodiment of the present invention. The method includes the steps of providing a questionnaire 58 that contains at least one question in regard to location of pain, at least one question in regard to level of pain, at least one question in regard to quality of pain, and at least one question in regard to frequency of pain; recording responses to said questions in said questionnaire 60; providing a set of integration grids that assign a level of impact to a plurality of body regions from said responses 62; calculating a weighted average of level of impact for said plurality of body regions 64; generating a scaled score 66 from said weighted average of level of impact for a plurality of body regions, wherein said weighted average of level of impact for a plurality of body regions is based at least in part by a distance from a location of pain, and wherein said weighted average of level of impact for said plurality of body regions is based at least in part by a body mass index. The method further comprises the step of suggesting a treatment to reduce a musculoskeletal disorder risk based on at least in part on said scaled score 68; the step of generating an overall scaled score 70 from said weighted average of level of impact from the plurality of body regions; or generating a quantification of musculoskeletal disorder risk 72.

In the case of a Question/Answer associated with multiple regions of the body, the risk values associated with it maybe defined differently for each region.

There are 6 areas of the spine. Some Questions/Answers are associated with one or more of these areas.

Example Initial Values Used in Scoring

1. Weights—In performing weighted averages, the following values could be used:
   (H)igh values=3
   (M)edium values=2
   (L)ow values=1
2. Joint/Spine Priority—In applying joint priority values, the following factors could be used:
   Priority 1 Joints=100%
   Priority 2 Joints=60%
   Priority 3 Joints=40%
   Priority 4 Joints=20%
   Priority 5 & 6 Joints=20%
3. Score Evaluation—the following ranges will be used to translate numeric scores into scores of H, M and L. Note: at this point there is only one set of ranges used for all areas of scoring.
   L=0-0.46
   M=0.47-0.74
   H=0.75-1
4. Ideal BMI=24.9

Explanation of Notation & Formulas

Provided below is a summary of the notation used in the definition of Example calculations:

| | |
|---|---|
| $W_1$ | Highest Weight Value |
| $W_2$ | Second highest Weight Value |
| $W_3$ | Third highest Weight Value |
| $H_\#$ | Number of High Values |
| $M_\#$ | Number of Medium Values |
| $L_\#$ | Number of Low Values |
| $T_\#$ | Total number of High, Medium and Low Values |
| $J_1$-$J_5$ | Score associated with Joints 1-5 |
| $J_{1f}$-$J_{5f}$ | Joint Priority Factor associated with a Joints 1-5 |
| $S_1$-$S_5$ | Value associated with Spine Areas 1-5 |
| $S_{1f}$-$S_{5f}$ | Spine Priority Factor associated with a Spine Areas 1-5 |
| BMI | Body Mass Index |
| IBMI | Ideal BMI |
| BMIF | Ratio of BMI to IBMI |

Formulas:

Region Score=$(W_1{*}H_\#)+(W_2{*}M_\#)+(W_3{*}L_\#)/(W_1{*}T_\#)$

Joint Score=$(W_1{*}H_\#)+(W_2{*}M_\#)+(W_3{*}L_\#)/(W_1{*}T_\#)$

Spine Area Score=$(W_1{*}H_\#)+(W_2{*}M_\#)+(W_3{*}L_\#)/(W_1{*}T_\#)$

Upper Joint Impact=$(J_1{*}J_{1f})+(J_2{*}J_{2f})+(J_3{*}J_{3f})+(J_4{*}J_{4f})/(W_1{*}(J_{1f}+J_{2f}+J_{3f}+J_{4f}))$ Lower Joint Impact=$(J_1{*}J_{1f})+(J_2{*}J_{2f})+(J_3{*}J_{3f})+(J_4{*}J_{4f})+{*}(J_5{*}J_{5f})/(W_1{*}(J_{1f}+J_{2f}+J_{3f}+J_{4f}+J_{5f}))$ Spine Impact=$(S_1{*}S_{1f})+(S_2{*}S_{2f})+(S_3{*}S_{3f})+(S_4{*}S_{4f})+(S_5{*}S_{5f})+(S_6{*}S_{6f})/(W_1{*}(S_{1f}+S_{2f}+S_{3f}+S_{4f}+S_{5f}+S_{6f}))$ BMI=$((Weight/(Height^2)){*}703)$

BMIF=BMI/IBMI

I. Analysis Process

A. Initial Review

1. Identify Chief Complaint

The participant's chief complaint is derived from answers to the section of a questionnaire containing an anatomical chart.

These questions are identified in the MSD Matrix with a numeric value in the "Anatomic Reference" column. The value in this column refers to the specific body part for which that question references. These values refer to MSD Matrix and the Anatomic Reference Summary.

This section of the questionnaire asks the participant to describe any pain they have, the quality of the pain (dull, burning sharp etc), how frequently they have the pain, if they have been treated for the problem and the severity of the pain on a scale of 0-10 with 10 being the highest.

The chief complaint is determined by reviewing the answers in the following priority:

1. Identify the body part(s) with the most severe pain based on the Visual Analog Scale (VAS) of 0-10 where 0 is no pain, 10 being the most pain ever felt.
2. If there is more than one body part with an equal amount of pain, select the one(s) in which there has been treatment or surgery.
3. If there is still more than one, select the one(s) which occur most frequently.

4. If there is still more than one, select the one(s) where the quality of pain is the most significant. Significance of pain from highest to lowest is: Sharp, Burning, Dull, Stiffness)

If this process yields more than one chief complaint then process the questionnaire once for each chief complaint yielding an individual report for each.

The result of this process is the individual's Chief Complaint.

2. Identify Primary Joint of Involvement

Each point on the anatomical chart is associated with a specific joint system.

Using the "Anatomic Reference Summary" the Chief Complaint using either the "Anatomic Reference" column or the "Anatomic Name" column.

The corresponding joint in the "Primary Joint" column is the Primary Joint of Involvement.

Example

| Anatomic Reference | Anatomic Name | Primary Joint |
|---|---|---|
| 1 | Head | Neck |
| 2 | Upper Trapezius (Front) | Neck |
| 3 | Shoulder | S, UT, M-B, Scap |

Using an excerpt from the chart, if the Head is the Chief Complaint, the Neck is the Primary Joint of Involvement.

3. Identify Primary Area of Involvement

Each point on the anatomical chart is associated with one or more of the 4 body regions.

Using the "Anatomic Reference Summary" identify the Chief Complaint using either the "Anatomic Reference" column or the "Anatomic Name" column.

The corresponding body region(s) located under the heading "Region Impact" is the Primary Area of Involvement.

It is possible for there to be more than one corresponding regions related to a chief complaint.

In this event, the outcome of the Region Analysis and that of the complicating factors would have the same effect on each of the applicable Areas of Involvement.

Example

| Anatomic Reference | Anatomic Name | Primary Joint |
|---|---|---|
| 1 | Head | Neck |
| 2 | Upper Trapezius (Front) | Neck |
| 3 | Shoulder | S, UT, M-B, Scap |

Using an excerpt from the chart, if the Head is the Chief Complaint, the Neck is the Primary Joint of Involvement.

B. Calculate Initial Region Score

This analysis will be performed 4 times. Once for each joint system.

1. Group Responses by Region and level of impact

Each question/answer is associated with one or more body regions and each of these is assigned a level of impact in the form of None (blank), 0, L, M or H.

The starting point in determining the region score is to group answers by the applicable region then by the level of impact.

2. Perform Weighted Average for Each Region

A value is assigned to each answer based on the level of impact. The level of impact for each region/question/answer is found in the MSD Matrix Summary.

Answers with a high "H" impact are given more weight in this calculation and thus are assigned a higher value ($W_1$). Answers with a medium "M" impact and those with a low "L" impact are given less weight ($W_2$ $W_3$ respectively). Questions with no impact on the region and questions with "0" impact on the region are discarded.

Calculation is as follows:

Region Score=$(W_1*H_\#)+(W_2*M_\#)+(W_3*L_\#)/W_1*T_\#$

Example

| Questions | Impact | Weighted Value |
|---|---|---|
| Q1 | H | 3 |
| Q2 | H | 3 |
| Q3 | M | 2 |
| Q4 | M | 2 |
| Q5 | M | 2 |
| Q6 | L | 1 |
| Q7 | L | 1 |
| Q8 | L | 1 |

Weight Values:
$W_1$=3
$W_2$=2
$W_3$=1

Score Totals:
Number of High Values ($H_\#$)=2
Number of Medium Values ($M_\#$)=3
Number of Low Values ($L_\#$)=3
Total Number of Values ($T_\#$)=8

Calculation:
Region Score=$(W_1*H_\#)+(W_2*M_\#)+(W_3*L_\#)/(W_1*T_\#)$
Region Score=$(3*2)+(2*3)+(1*3)/(3*8)$
Region Score=15/24
Region Score=0.63

3. Result of Weighted Average=Region Score

The numeric value of the region score is then converted back into a value of "L", "M" or "H".

From section ID3—Initial Values Used in Scoring:
If the numeric region score is 0.3-0.46 then the Region Score=Low
If the numeric region score is 0.47-0.74 then the Region Score=Med
If the numeric region score is 0.75-1 then the Region Score=High In this example, the numeric region score of 0.63 would assign this region a score of Medium.

C. Identify & Score Complicating Factors

1. Bio-Mechanical Analysis (Joints)

a) Joints (1) Group Responses by Joint and level of Impact

The focus of the Joint Analysis are those joints associated with the Primary Area of Involvement.

If the Primary Area of involvement is the Neck or Upper Extremities, the joint analysis will review Upper Joints (Neck, Shoulder, Upper Trap, Mid Back, Scapula, Elbow, Wrist and Hand).

If the Primary Area of involvement is the Back or Lower Extremities, the joint analysis will review Lower Joints (Lower Back, Hip, Knee, Ankle and Foot).

Each question/answer is associated with a joint.

Group questions/answers by their associated joint then by level of impact on the Primary Area of Involvement. If there is more than one Primary Area of Involvement, the entire Bio-Mechanical Analysis will be performed for each Area.

Discard any questions/answers having no impact on the Primary Area of Involvement (blank or value of 0).

(2) Perform Weighted Average for Each Joint

This weighted average is performed for each of the applicable joints.

A value is assigned to each answer based on the level of impact in the Primary Area of Involvement unless there is also a value in the "Impact" column under the heading "Mechanics—Joint". In this case, use the value found in the Impact column of the Mechanics—Joint heading.

See "Sample Grid" in the example below.

Answers with a high "H" impact are given more weight in this calculation and thus are assigned a higher value. Questions with no impact on the region and questions with "0" impact on the region are discarded.

Calculation is as follows:

Joint Score=$(W_1*+(W_2*+(W_3*/(W_1*T_\#))$

See "Example Calculation" in the example below.

The numeric value of each Joint score is then converted back into a value of "L", "M" or "h".

From section ID3—Initial Values Used in Scoring:
If the numeric score is 0.3-0.46 then the Joint Score=Low
If the numeric score is 0.47-0.74 then the Joint Score=Med
If the numeric score is 0.75-1 then the Joint Score=High Example Sample Grid:

| QA ID | Questions | Answers | Region Impact Neck | Mechanics - Joint Primary | Impact |
|---|---|---|---|---|---|
| 125 | Anatomic/Head-Quality | None | 0 | Neck | |
| 126 | Anatomic/Head - Quality | Dull | 0 | Neck | |
| 127 | Anatomic/Head - Quality | Burning | 0 | Neck | |
| 128 | Anatomic/Head - Quality | Sharp | 0 | Neck | H |
| 129 | Anatomic/Head - Numbness | Yes | H | Neck | |

In this example, QA ID 128 has a value in the Mechanics-Joint/Impact cell. The impact value in this cell is used instead of the value in the Region Impact cell. QA ID 129 has no value in the Mechanics-Joint/Impact cell therefore, the value in the Region Impact cell is used Example Calculation:

| Joint | Impact | Weighted Value |
|---|---|---|
| Wrist/Hand | H | 3 |
| Wrist/Hand | H | 3 |
| Wrist/Hand | M | 2 |
| Wrist/Hand | M | 2 |
| Wrist/Hand | M | 2 |
| Wrist/Hand | L | 1 |
| Wrist/Hand | L | 1 |
| Wrist/Hand | L | 1 |

Weight Values:
$W_1=3$
$W_2=2$
$W_3=1$

Score Totals:
Number of High Values ($H_\#$)=2
Number of Medium Values ($M_\#$)=3
Number of Low Values ($L_\#$)=3
Total Number of Values ($T_\#$)=8

Calculation:
Joint Score=$(W_1*h_\#)+(W_2*M_\#)+(W_3*l_\#)/(W_1*T_\#)$
Joint Score=$(3*2)+(2*3)+(1*3)/(3*8)$
Joint Score=15/24
Joint Score=0.63
0.63="M" for this Joint (3) Calculate Joint Impact To calculate the total impact of the joints on the Primary Area of Involvement, the individual joint scores are again weighted and averaged giving more consideration to the joints closest to the Primary Joint of Involvement and less to those furthest away.

The Primary Joint of Involvement has the highest priority. The remainder of the Joint Priorities are assigned based on how far away (distal) those joints are.

There is a different joint priority for Upper Joints and Lower Joints, otherwise the calculation is the same.

A Joint Integration Grid (JIG) is used to determine the priority.

JIGs

Upper Joint JIG:

| Joint | Priority | | | |
|---|---|---|---|---|
| Neck | 1 | 4 | 3 | 2 |
| Shoulder Upper Trap Mid Back Scapula | 2 | 3 | 2 | 1 |
| Elbow Wrist | 3 | 2 | 1 | 2 |
| Hand | 4 | 1 | 2 | 3 |

In this example; the Elbow/Wrist is the Primary Joint of Involvement. Therefore, Shoulder/Upper Trap/Mid Back/Scapula and Hand are both Priority 2 Joints. Neck is a Priority 3 Joint. There is no Priority 4 Joint.

Lower Joint JIG:

| Joint | Priority | | | | |
|---|---|---|---|---|---|
| Lower Back | 1 | 5 | 4 | 3 | 2 |
| Hip | 2 | 4 | 3 | 2 | 1 |
| Knee | 3 | 3 | 2 | 1 | 2 |
| Ankle | 4 | 2 | 1 | 2 | 3 |
| Foot | 5 | 1 | 2 | 3 | 4 |

In this example; the Foot is the Primary Joint of Involvement. Therefore, Ankle is the Priority 2 Joint. Knee is the Priority 3 Joint. Hip is the Priority 4 Joint. Lower Back is the Priority 5 Joint.

(a) Upper Joints

When calculating a score for upper joints, a score of "L", "M" or "H" will have been calculated for each of the 4 joints associated with the upper joints.

These values are converted into numeric representations based on the weights associated with the joint score.

High=3, M=2, L=1

Identify the column in the Upper JIG where the Primary Joint of Involvement is listed as "1". The score for this joint will be weighted the highest. Looking at the same column, the joint(s) identified with a priority of "2" will be weighted the second highest following through to the fourth joint.

Upper Joint Impact=$(J_1*J_{1f})+(J_2*J_{2f})+(J_3*J_{3f})+(J_4*J_{4f})/(W_1*(J_{1f}+J_{2f}+J_{3f}+J_{4f}))$ Note: In some cases, there are not 4 priorities (see the last two columns of the JIG above). In this case, the formula is modified using the same factor for joints with the same priority. For example, the formula for the last column would look like this:

Upper Joint Impact=$(J_1*J_{1f})+(J_2*J_{2f})+(J_2*J_{2f})+(J_3*J_{3f})/(W_1*J_{2f}+J_{2f}+J_{3f}))$ Example For the purposes of the example below, we will assume the Elbow/Wrist is our Primary Joint of Involvement. In this case, the Hand, Shoulder/Upper Trap/Mid Back/Scapula are priority 2 joints. The Neck is a priority 3 joint. There is no Priority 4 joint.

| Joint | Priority | | | |
|---|---|---|---|---|
| Neck | 1 | 4 | 3 | 2 |
| Shoulder Upper Trap Mid Back Scapula | 2 | 3 | 2 | 1 |
| Elbow Wrist | 3 | 2 | 1 | 2 |
| Hand | 4 | 1 | 2 | 3 |

If the initial joint scores were:
Elbow/Wrist="H"
Hand="M"
Shoulder/Upper Trap, Mid Back, Scapula="M"
Neck="L"

The scoring would look like this:

| Joint | Joint Score | Weight | Joint Priority Factor |
|---|---|---|---|
| Elbow/Wrist | H | $(J_1)$ = 3 | $(J_{1f})$ = 100% |
| Hand | M | $(J_2)$ = 2 | $(J_{2f})$ = 60% |
| Shoulder/UT/MB/Scap | M | $(J_2)$ = 2 | $(J_{2f})$ = 60% |
| Neck | L | $(J_3)$ = 1 | $(J_{3f})$ = 40% |

Upper Joint Impact=$(J_1*J_{1f})+(J_2*J_{2f})+(J_2*J_{2f})+(J_3*J_{3f})/(W_1*(J_{1f}+J_{2f}+J_{2f}+J_{3f}))$ Upper Joint Impact=$(3*1)+(2*0.6)+(2*0.6)+(1*0.4)/(3*(1+0.6+0.6+0.4))$ Upper Joint Impact=3+1.2+1.2+0.4/3*2.6

Upper Joint Impact=5.8/7.8

Upper Joint Impact=0.74

*Note: In the example above 2 joint systems had the same priority. The calculation of the total possible score used a weight value of 3 times the percentages of 100, 60, 60 and 40 versus the typical percentages of 100, 60, 40 and 20.

Joint scores of 0.3-0.46="L", 0.47-74="M", 0.75-1="H". The score for this joint would be (b) Lower Joints When calculating a score for lower joints, a score of "L", "M" or "H" will have been calculated for each of the 4 joints associated with the upper joints.

These values are converted into numeric representations based on the weights associated with the joint score.

High=3, M=2, L=1

Identify the column in the Lower JIG where the Primary Joint of Involvement is listed as "1". The score for this joint will be weighted the highest. Looking at the same column, the joint(s) identified with a priority of "2" will be weighted the second highest following through to the fifth joint.

Lower Joint Impact=$(J_1*J_{1f})+(J_2*J_{2f})+(J_3*J_{3f})+(J_4*J_{4f})+(J_5*J_{5f})/(W_1*(J_{1f}+J_{2f}+J_{3f}+J_{4f}+J_{5f}))$ Note: In some cases, there are not 5 priorities (see the last three columns of the JIG above). In this case, the formula is modified using the same factor for joints with the same priority. For example, the formula for the last column would look like this:

Lower Joint Impact=$(J_1*J_{1f})+(J_2*J_{2f})+(J_2*J_{2f})+(J_3*J_{3f})/(W_1*(J_{1f}+J_{2f}+J_{2f}+J_{3f}))$ Example For the purposes of the example below, we will assume the Foot is our Primary Joint of Involvement. In this case, the Ankle is a priority 2 Joint. The Knee is a priority 3 joint. The Hip is a Priority 4 joint and the Lower Back is a Priority 5 Joint.

| Joint | Priority | | | | |
|---|---|---|---|---|---|
| Lower Back | 1 | 5 | 4 | 3 | 2 |
| Hip | 2 | 4 | 3 | 2 | 1 |
| Knee | 3 | 3 | 2 | 1 | 2 |
| Ankle | 4 | 2 | 1 | 2 | 3 |
| Foot | 5 | 1 | 2 | 3 | 4 |

If the initial joint scores were:
Foot="H"
Ankle="M"
Knee="M"
Hip="L"
Lower Back="L"
The scoring would look like this:

| Joint | Joint Score | Weight | Joint Priority Factor |
|---|---|---|---|
| Foot | H | $(J_1) = 3$ | $(J_{1f}) = 100\%$ |
| Ankle | M | $(J_2) = 2$ | $(J_{2f}) = 60\%$ |
| Knee | M | $(J_3) = 2$ | $(J_{3f}) = 40\%$ |
| Hip | L | $(J_4) = 1$ | $(J_{4f}) = 20\%$ |
| Lower Back | L | $(J_5) = 1$ | $(J_{5f}) = 20\%$ |

Lower Joint Impact=$(J_1*J_{1f})+(J_2*J_{2f})+(J_3*J_{3f})+(J_4*J_{4f})+(J_5*J_{5f})/(W_1*(J_{1f}+J_{2f}+J_{3f}+J_{4f}+J_{5f}))$
Lower Joint Impact=$(3*1)+(2*0.6)+(2*0.4)+(1*0.2)+(1*0.2)/(3*(1+0.6+0.4+0.2+0.2))$
Lower Joint Impact=$3+1.2+0.8+0.2+0.2/3*2.4$
Lower Joint Impact=$5.4/7.2$
Lower Joint Impact=$0.75$ (4) Determine the Overall Joint Score
1. In the case of the Upper Joints, the Overall Joint Score=Upper Joint Impact.
2. In the case of the Lower Joints, an additional factor is applied based on the participants Body Mass Index (BMI). Simply put, people who are overweight put more stress on their lower joints than people who are not.
Calculate the participant's BMI:
BMI=((Weight/Height$^2$)*703)
Calculate the BMIF:
BMIF=BMI/IBMI
Apply the BMIF to the Lower Joint Impact Score:
Overall Joint Impact Score=Lower Joint Impact Score*BMIF b) Spine Analysis
The spine is divided into 6 distinct areas. From top to bottom, they are: Occipital, Cervical, Thoracic, Lumbar, Sacral and Pelvic.
This analysis is conditional. If there are 2 ore more responses associated with a Spine Area with an impact of L, M or H then perform the analysis.
The analysis is similar to the region analysis where a weighted average is performed on each of the spinal areas then combined with the findings of the Joint Analysis to get a comprehensive result of the participants bio mechanics.
References to the spinal regions can be found in the Spine Impact columns of the MSD Matrix and in the Spine Impact columns of the Anatomic Reference Summary.

(1) Group Responses by Spinal Area and level of impact
There are six areas of the spine: Occipital, Cervical, Thoracic, Lumbar, Sacral and Pelvis.
Only some questions/answers are associated with a spinal region.
The Spinal Analysis is conditional. It is performed if the Chief Complaint falls into one of the six areas and there is a positive response with an impact value of L, M or H to any other question associated with the six areas of the spine.
Group questions/answers by spinal area and level of impact.
Discard any questions/answers having no impact on one of the spinal areas (blank or value of 0).
If the criteria is met, continue with the spinal analysis.
(2) Perform Weighted Average for Each Spinal Region
This weighted average is performed for each of the Spinal Area.
A value is assigned to each answer based on the level of impact. The level of impact for each spine area/question/answer is found in the MSD Matrix.
Answers with a high "H" impact are given more weight in this calculation and thus are assigned a higher value. Questions with no impact on the Spinal Area are discarded.
Calculation is as follows:
Spine Area Score=$(W_1*H_\#)+(W_2*M_\#)+(W_3*L_\#)/(W_1*T_\#)$
The numeric value of each Joint score is then converted back into a value of "L", "M" or "H".
From section ID3—Initial Values Used in Scoring:
If the numeric score is 0.3-0.46 then the Joint Score=Low
If the numeric score is 0.47-0.74 then the Joint Score=Med
If the numeric score is 0.75-1 then the Joint Score=High Example
Example Calculation:.

| Spinal Area | Impact | Weighted Value |
|---|---|---|
| Occipital | H | 3 |
| Occipital | H | 3 |
| Occipital | M | 2 |
| Occipital | M | 2 |
| Occipital | M | 2 |
| Occipital | L | 1 |
| Occipital | L | 1 |
| Occipital | L | 1 |

Weight Values:
$W_1=3$
$W_2=2$
$W_3=1$
Score Totals:
Number of High Values $(H_\#)=2$
Number of Medium Values $(M_\#)=3$
Number of Low Values $(L_\#)=3$
Total Number of Values $(T_\#)=8$
Calculation:
Spine Area Score=$(W_1*H_\#)+(W_2*M_\#)+(W_3*(L_\#)/(W_1*T_\#)$
Spine Area Score=$(3*2)+(2*3)+(1*3)/(3*8)$
Spine Area Score=$15/24$
Spine Area Score=$0.63$
0.63="M" for this Spinal Area (3) Calculate Spine Impact To calculate the total impact of the Spine, the individual Spine Area scores are again weighted and averaged giving more or less weight based on the Spinal Integration Grid (SIG) below.

When calculating a score for Spinal Areas, a score of "L", "M" or "H" will have been calculated for one or more of the 6 applicable areas. Note: It is possible that not all areas will have an impact.

These values are converted into numeric representations based on the weights associated with the score.

High=3, M=2, L=1

Identify the Spinal Area corresponding to the Primary Joint of Involvement.

Locate the column in the SIG where this Spinal Area is listed as "1". The score for this area will be weighted the highest. Looking at the same column, the areas identified with a priority of "2" will be weighted the second highest following through to the last area.

Spine Impact=$(S_1*+S_{1f})+(S_2*S_{2f})+(S_3*S_{3f})+(S_4*S_{4f})+(S_5*S_{5f})+(S_6*S_{6f})/(W_1*(S_{1f}+S_{2f}+S_{3f}+S_{4f}+S_{5f}+S_{6f}))$ Note: In some cases, there are not 5 separate priorities (see the last two columns of the JIG above). In this case, the formula is modified using the same factor for joints with the same priority. For example, the formula for the last column would look like this:

Spine Impact=$(S_1*S_{1f})+(S_2*S_{2f})+(S_2*S_{2f})+(S_2*S_{2f})+(S_3*S_{3f})+(S_4*S_{4f})/(W_1*(S_{1f}+S_{2f}+S_{2f}+S_{2f}+S_{3f}+S_{4f}))$ Example
Spinal Integration Grid (SIG):

| | Spinal Area | | | Priority | | |
|---|---|---|---|---|---|---|
| Upper | Occipital | 1 | 2 | 3 | 4 | 2 |
| | Cervical | 2 | 1 | 2 | 3 | 4 |
| | Thoracic | 3 | 2 | 1 | 2 | 3 |
| Upper | Lumbar | 4 | 3 | 2 | 1 | 2 |
| | Sacral | 2 | 4 | 3 | 2 | 1 |
| | Pelvis | 3 | 5 | 4 | 2 | 2 |

Example Calculation:

If the initial spine area scores were as listed below and the Chief Complaint was in the Occipital Spine Area:

Occipital="H"
Cervical="M"
Thoracic="M"
Lumbar="L"
Sacral="L"
Pelvis="M"

The scoring would look like this:

| Spine Area | Spine Area Score | Weight | Spine Priority Factor |
|---|---|---|---|
| Occipital | H | $(S_1) = 3$ | $(S_{1f}) = 100\%$ |
| Cervical | M | $(S_2) = 2$ | $(S_{2f}) = 60\%$ |
| Thoracic | M | $(S_3) = 2$ | $(S_{3f}) = 40\%$ |
| Lumbar | L | $(S_4) = 1$ | $(S_{4f}) = 20\%$ |
| Sacral | L | $(S_5) = 1$ | $(S_{5f}) = 20\%$ |
| Pelvis | M | $(S_6) = 2$ | $(S_{6f}) = 20\%$ |

Spine Impact=$(S_1*S_{1f})+(S_2*S_{2f})+(S_3*S_{3f})+(S_4*S_{4f})+(S_5*S_{5f})+(S_6*S_{6f})/(W_1*(S_{1f}+S_{2f}+S_{3f}+S_{4f}+S_{5f}+S_{6f}))$ Spine Impact=$(3*1)+(2*0.6)+(2*0.4)+(1*0.2)+(1*0.2)+(2*0.2)/(3*(1+0.6+0.4+0.2+0.2+0.2))$
Spine Impact=3+1.2+0.8+0.2+0.2+0.4/3*2.6
Spine Impact=5.8/7.8
Spine Impact=0.74 c) Determine Overall Bio-Mechanical Score

If the Spine Analysis was performed, then the Overall Score for the Bio-Mechanic Analysis is the simple average of the Overall Joint Score and the Spine Impact Score.

If the Spine Analysis was not performed, then the Overall Score for the Bio-Mechanic Analysis is the Overall Joint Score.

The numeric value of Bio-Mechanic Score is then converted into a value of "L", "M" or "H".

From section ID3—Initial Values Used in Scoring:

If the Joint Impact Score is 0.3-0.46 then the Overall Joint Score=Low

If the Joint Impact Score is 0.47-0.74 then the Overall Joint Score=Med

If the Joint Impact Score is 0.75-1 then the Overall Joint Score=High d) Impact on Primary Area of Involvement If the overall score for the Bio mechanic Analysis is "H", increase the score by 1. List the joint responses under complicating Factors by priority.

2. Sensory (Nerves)

Burning or dull pain in the neck combined with numbness in one or both arms=High score for Upper Extremities.

Burning or dull pain in the lower back combined with numbness in one or both legs=High score for Lower Extremities.

Any finding of numbness in an extremity (arms, hands, legs, feet)=High score for the associated region.

Numbness in all four extremities (arms, hands, legs, feet)—High Overall score.

Bi-lateral tingling/numbness in the hands (both hands) or feet (both feet)=High Overall score where "Bi-lateral means any tingling or numbness in both hands or both feet regardless of the digits"

Positive responses to Biometric questions that indicate a high risk in the sensory column equals a H for the region and H for Overall score D. Determine Impact of Systemic Responses Systemic questions have an impact on the entire body and therefore positive responses to these questions will impact the Overall MSD Risk Score.

1. Select responses to questions with a corresponding value of L, M or H in the proper column of the MSD Matrix.

2. Group responses by level of impact.

3. Perform a weighted average in the same manner as the one done for a region.

4. The result of the weighted average uses the same scale to determine a value of "H", "M" or 5. A value of "H" for Systemic questions will increase the Overall MSD Risk score to "High" regardless of what it was previously.

E. Determine Impact of Trump Values

Questions marked as "Trump" override all calculations for a region and make that region "H". An example of a "Trump" value would be an indication of past surgery, which would result in an Overall Risk Score of High.

F. Calculate the Final Overall & Region Scores

Overall Score=Highest Region Score plus any additional effect of:
Region Analysis
Complicating Factors
Systemic Analysis
Trump Values Positive response to questions which contra-indicate the biometrics testing result in an Overall Score of High, no score for the regions and referral to the person's physician or healthcare provider.

The actual values used will depend upon the data sets used and construction of the matrices. It should be apparent to those skilled in the art how to construct such matrices which will vary depending on application, accuracy and precision. That is a simple questionnaire and matrices could be constructed, but may have poor accuracy and precision though be quick and inexpensive to use. The analysis is preferably performed with the use of at least one micro processor at some point in the process.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What is claimed is:

1. A method of assessing musculoskeletal disorder risk, comprising the steps of:
    providing a questionnaire that contains at least one question in regard to location of pain, at least one question in regard to level of pain, at least one question in regard to quality of pain, and at least one question in regard to frequency of pain;
    recording responses to said questions in said questionnaire;
    providing a set of integration grids that assign a level of impact to a plurality of body regions from said responses; implementing a processor to calculate a weighted average of level of impact for said plurality of body regions; implementing a processor to generate a scaled score from said weighted average of level of impact for a plurality of body regions, wherein said weighted average of level of impact for a plurality of body regions is based at least in part by a distance from a location of pain,
    providing a set of integration grids that assign a level of impact to said plurality of body regions from said responses;
    calculating a weighted average of level of impact for said plurality of body regions;
    generating a scaled score from said weighted average of level of impact for a plurality of body regions, wherein said weighted average of level of impact for said plurality of body regions is based at least in part by a distance from a location of pain and wherein said weighted average of level of impact for said plurality of body regions is based at least in part by a body mass index.

2. The method of claim 1, wherein said set of integration grids allows for assessing relationships between and within body regions.

3. The method of claim 1, wherein the method yields a quantification of musculoskeletal disorder risk within a body region.

4. The method of claim 1, further comprising the step of suggesting a treatment to reduce a musculoskeletal disorder risk based on at least in part on said scaled score.

5. The method of claim 1, wherein the step of providing a questionnaire additionally contains at least one question in regard to sensory symptoms.

6. The method of claim 5, further comprising the step of suggesting a treatment to reduce a musculoskeletal disorder risk based on at least in part on said scaled score.

7. The method of claim 1, wherein the step of providing a questionnaire additionally contains at least one question in regard to numbness.

8. The method of claim 1, wherein the method yields a quantification of musculoskeletal disorder risk.

9. The method of claim 1, further comprising the step of generating an overall scaled score from said weighted average of level of impact from said plurality of body regions.

* * * * *